United States Patent [19]

Dolbeare

[11] 4,345,027

[45] Aug. 17, 1982

[54] FLUOROMETRIC METHOD OF QUANTITATIVE CELL MUTAGENESIS

[75] Inventor: Frank A. Dolbeare, Livermore, Calif.

[73] Assignee: The United States of America as represented by the United States Department of Energy, Washington, D.C.

[21] Appl. No.: 215,767

[22] Filed: Dec. 12, 1980

[51] Int. Cl.³ .............................................. G01N 1/30
[52] U.S. Cl. ........................................ 435/21; 435/6; 424/7; 427/4
[58] Field of Search .................... 424/7, 8; 435/21, 9, 435/7, 172, 6; 250/461 B; 427/4

[56] References Cited

FOREIGN PATENT DOCUMENTS 4061 9/1979 European Pat. Off. ................ 424/7

OTHER PUBLICATIONS

Chem. Abs. vol. 85, 1976, 85:188687m.
Nature vol. 260, 1976, pp. 448–451.
Nature vol. 251, 1974 pp. 156–158.
Biochemical Genetics 1:61–64 (1967).
Pioc. Nat. Acad.-Sci. USA vol. 72, No. 2, pp. 493–497 2-75.

*Primary Examiner*—William F. Smith
*Attorney, Agent, or Firm*—Marvin J. Marnock; Roger S. Gaither; Richard G. Besha

[57] ABSTRACT

A method for assaying a cell culture for mutagenesis is described. A cell culture is stained first with a histochemical stain, and then a fluorescent stain. Normal cells in the culture are stained by both the histochemical and fluorescent stains, while abnormal cells are stained only by the fluorescent stain. The two stains are chosen so that the histochemical stain absorbs the wavelengths that the fluorescent stain emits. After the counterstained culture is subjected to exciting light, the fluorescence from the abnormal cells is detected.

10 Claims, No Drawings

FLUOROMETRIC METHOD OF QUANTITATIVE CELL MUTAGENESIS

The United States Government has rights in this invention pursuant to Contract No. W-7405-ENG-48 between the U.S. Department of Energy and the University of California.

BACKGROUND OF THE INVENTION

The present invention relates generally to quantitative cell mutagenesis, and more particularly to a fluorometric method of quantitative cell mutagenesis.

Quantitative mutagenesis in a cell culture can be determined by staining the culture with a colorimetric or histochemical stain, followed by observance of the adsorption curve obtained utilizing a measuring instrument such as a spectrophotometer. For example, if the mutagenesis is caused by the absence of a specific enzyme in cells, the cell culture is first stained colorimetrically. The normal cells will exhibit absorbance at a particular wavelength, while the cells deficient in the enzyme will not be absorbing at this wavelength.

A colorimetric method of cell mutagenesis detection is described by A. Wajntal and R. DeMars in *Biochemical Genetics* 1:61–64 (1967). Specifically, a histochemical method for the detection of the enzyme glucose-6-phosphate dehydrogenase (G6PD) is described. Enzymatic reduction of NADP to NADPH in the presence of the substrate (glucose-6-phosphate) is coupled to the reduction of tetrazolium salts. Colored, insoluble deposits appear within cells containing the enzyme. A similar staining technique is described in *Proc. Nat. Acad. Sci. USA*, Vol. 72, No. 2, pp 493–497 (1975). The production of NADPH, and hence the presence of the G6PD, is determined by observing the increase in absorbence at 340 mm on a recording spectrometer. The assaying of adenine phosphoribosyltransferase (APRT) and hypoxanthine phosphoribosyltransferase (HPRT), utilizing a colorimetric staining method, is described by L. A. Chasin in *Cell*, 2, 37–41 (1974).

Colorimetric staining assay methods as described above include a number of serious disadvantages. Mutagenesis, e.g., cells deficient in a cellular compound, can be expected to occur typically once in a culture of 100,000 cells. With the methods described above, the absorbance at a particular wavelength of each cell is observed. Detection of the abnormal cell is dependent on the observance of a difference, such as a pronounced decrease in staining intensity, thereby pinpointing the mutagenetic cell. Noise signals inherent in all detection instruments tend to interfere in the detection. Thus the reliability of the results is suspect. Additionally, the colorimetric methods require plating and growing of clones which may take 10 days or more to achieve.

Instead of detecting a drop in colorimetric activity at an occurrence level of one out of every 100,000 cells, it is more desirable to detect only those cells where mutagenesis has occurred. Staining, followed by fluorescent counter-staining of cell cultures, provides such a detection method. This method permits cell assaying to be completed in approximately three hours, and minimizes problems associated with instrument background noise.

SUMMARY OF THE INVENTION

An object of the invention is to provide a method for determining mutagenesis in a cell culture.

Another object of the invention is to provide a method for determining mutagenesis in a cell culture by detecting the fluorescence of abnormal cells.

Still another object of the invention is to provide a method for determining cell mutagenesis quicker and with greater accuracy than methods previously known.

Additional objects, advantages, and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects, and in accordance with the purpose of the present invention, as embodied and broadly described herein, a method for assaying a cell culture for mutagenesis may comprise first staining the cell culture with a histochemical stain. The histochemical stain is chosen so that it stains only the normal cells and not the abnormal cells in the culture. The culture is counterstained with a fluorescent stain and then subjected to exciting light. Fluorescence from the counterstained culture is detected, and provides the measure of mutagenesis.

In a further aspect of the present invention, in accordance with its objects and purposes, the method for assaying a cell culture for mutagenesis, characterized by abnormal cells being deficient in a cellular compound found in normal cells, may comprise applying a histochemical stain to the cell culture. The histochemical stain stains only the normal cells and causes them to become colored. A fluorescent stain is applied which stains both the normal and abnormal cells. The two strains are chosen so that the histochemical stain absorbs the wavelengths which the fluorescent stain emits, thereby yielding detectable fluorescence only in the abnormal cells. The counterstained culture is subjected to exciting light, and the fluoresence from the abnormal cells is detected.

Mutagenesis in cells is detected, as disclosed by the method of the invention, by measuring the fluorescence of abnormal cells in a counterstained cell culture. Compared to prior art colorimetric methods, wherein a change in absorbence of the abnormal cells is detected, the method of the present invention minimizes problems associated with instrument background noise. Additionally, the counterstaining method of the invention provides complete assaying in a greatly reduced time frame compared to traditional colormetric techniques, typically about three hours.

DETAILED DESCRIPTION OF THE INVENTION

In accordance with the invention, a method for assaying a cell culture to detect abnormal cells is described. Abnormal cells, as used in this context, are defined as being deficient in some cellular material, which may include enzymes, proteins, carbohydrates, lipids, DNA, and the like. A histochemical stain is first applied to the cell culture. The histochemical stain is sensitive to the presence of the cellular material, and therefore stains only the normal cells. A fluorescent stain is then applied to the cell culture, staining both the normal and abnormal cells. Proper choice of the fluorescent stain is imperative. It is required that the histochemical stain absorb substantially at the wavelengths emitted by the fluorescent stain. In effect, the histochemical stain quenches the fluorescent one, with the result that only the abnormal cells will fluoresce. Following the counterstaining, exciting light is caused to fall incident on the cell culture, and the resulting fluorescence of the abnormal cells is detected.

The assaying method disclosed herein is essentially a staining/counterstaining method, e.g., a histochemical stain is first applied to a cell culture, and then a fluorescent stain is applied. It is necessary, however, to coordinate the absorption and transmittance characteristics of the histochemical and fluorescent stains. The histochemical stain must absorb the wavelengths that the fluorescent stain emits.

Consider, for example, use of the histochemical stain NADP plus nitroblue tetrazolium (NBT)-3,3'(4,4'-di-o-anisylene)-2,2'-di(p-nitrophenyl)-bis(5-phenyl)-di-tetrazolium chloride. In the presence of the enzyme G6PD, NADP is reduced to NADPH, which in turn reduces NBT to a blue formazan which can be determined by noting the increase in the absorbance at 580 nm. To employ the method of the invention, the fluorescent stain chosen must emit light at around 580 nm. The normal cells which contain the enzyme G6PD will become stained with NBT (the histochemical stain) in that NBT is reduced to the formazan, whereas the abnormal cells which are deficient in the enzyme cannot reduce the NBT. Therefore, only the normal cells absorb at 580 nm. When the cell culture is subsequently counterstained with a fluorescent stain, e.g., chromomycin or fluoroscamine, both normal and abnormal cells become stained. However, since the normal cells are absorbing at substantially the same wavelength that the fluorescent stain is emitting, only the abnormal cells exhibit fluorescent behavior which is detectable.

Examples of histochemical stains which may be employed include nitroblue tetrazolium, tetranitro blue tetrazolium, thiocarbamyl nitroblue tetrazolium, distyryl nitroblue tetrazolium, fast blue B, fast blue BBN, fast red TR, and tetramethylbenzadine. The preferred histochemical staining solutions include nitroblue tetrazolium with phenazine methosulfate, fast blue BBN with naphthol AS-BI phosphate, and hydrogen peroxide with tetramethylbenzidine.

Specific examples of fluorescent counterstains which may be utilized include fluorescamine, fluorescein isothiocyanate (FITC), chromomycin A3, Hoechst 33342, Hoechst 3325, propidium iodide, acridine orange, and the like. The preferred fluorescent counterstaining solutions include chromomycin A3 solutions and fluorescamine solutions.

In one embodiment of the invention, a culture of cells is first washed, and then fixed with dilute glutaraldehyde, which serves to minimize cell rupture during automated cytology, and additionally helps to maintain the enzyme within the cell. Essentially, this provides cleaner cell staining. Cells are incubated and stained with a histochemical colorimetric stain. Subsequently, the cells are washed, centrifuged, and suspended in a fluorescent stain. The cells are subjected to exciting light in an instrument such as a flow cytometer, and the fluorescence detected. The entire process takes about three hours. When a flow cytometer is used, cells can be counted at a rate of from 5,000 to 10,000 cells per second. With the occurrence of abnormal cells at about one out of every 100,000, the flow cytometer can separate and detect an abnormal cell every 10 seconds. Additionally, the cells can be assayed by microscopy, microfluorometry, and fluorescence image analyzing.

The invention is a valuable tool for determining mutagenesis in cells, and in particular will find utility in cancer research. It provides a method of assay much quicker than prior art methods, and with greater reliability, since instrument noise does not interfere to an appreciable extent. Among the possible applications of the invention are: protein colorimetric stain, followed by a fluorescent DNA stain; enzyme colorimetric stain, followed by a fluorescent protein stain; a protein colorimetric stain employed with a metal fluorescent stain, and a lipid colorimetric stain used with a protein fluorescent stain. Mutagenesis leading to a protein, carbohydrate, lipid, enzyme, or DNA deficiency can be determined.

The following examples are illustrative of the invention, and are not to be regarded as limitative.

EXAMPLE 1

Chinese hamster ovary cells (CHO) were assayed for mutagenesis. A culture of CHO cells was centrifuged and suspended in isotonic saline buffered with 0.02 M sodium phosphate at pH 7.0. The cells were again centrifuged and the solution removed, followed by resuspension in a fixative solution of 0.2% glutaraldehyde in the phosphate-buffered saline for 30 minutes at 4° C. The cells were then removed from the fixative solution by centrifugation and resuspension in 1 ml of phosphate-buffered saline. 0.2 ml of the cell suspension was removed and the histochemical staining solution applied. The staining solution consisted of 0.02 M sodium phosphate in 0.15 M NaCl, 0.2 mM NADP, 0.2 mM nitroblue tetrazolium, 0.05 mM phenazine methosulfate (PMS) and 1 mM glucose-6-phosphate. The stained cells were then washed with cold (4° C.) 70% ethanol, followed by alcohol removal through centrifugation. The cells were resuspended in a second staining solution (chromomycin A3) comprising 10 mg chromomycin A3, 1.5 g $MgCl_2$ in 500 ml of distilled water. The cells were assayed by flow cytometry, revealing marked fluorescence in the mutant cells, while the normal cells were only very weakly fluorescent. The entire assay took less than three hours.

EXAMPLE 2

Chinese hamster ovary cells (CHO) were again assayed for G6PD deficiency. A culture of CHO cells was centrifuged and resuspended in isotonic saline buffered with 0.02 M sodium phosphate at pH 7.0. The cells were again centrifuged and the solution removed, followed by resuspension in a fixative solution of 0.2% glutaraldehyde in the phosphate-buffered saline for 30 minutes at 4° C. The cells were then removed from the fixative solution by centrifugation and resuspension in 1 ml of phosphate-buffered saline. 0.2 ml of the cell suspension was removed, and the histochemical staining solution applied. The staining solution consisted of 0.02 M sodium phosphate in 0.15 M NaCl, 0.2 mM nitroblue tetrazolium, 0.15 mM phenazine methosulfate (PMS) and 1 mM glucose-6-phosphate. The stained cells were then washed with cold (4° C.) 70% ethanol, followed by ethanol removal through centrifugation. The cells were resuspended in a second staining solution (fluorescamine) comprising 5 mg fluorescamine per liter of dry acetone. When assayed by flow cytometry, the normal cells were only weakly fluorescent, while the abnormal cells were highly fluorescent. The entire assay took less than three hours.

EXAMPLE 3

Bladder tumor cells may be deficient in one or more esterase enzymes, specifically alkaline phosphatase. Normal cells have high levels of this enzyme.

A culture of bladder cells was centrifuged, and resuspended in isotonic saline buffered with 0.02 M sodium phosphate at pH 7.0. The cells were again centrifuged and the solution removed, followed by resuspension in a fixative solution of 0.2% glutaraldehyde in the phosphate-buffered saline for 30 minutes at 4° C. The cells were then removed from the fixative solution by centrifugation and resuspension in 1 ml of phosphate-buffered saline. 0.2 ml of the cell suspension was removed, and alkaline phosphate histochemical staining solution applied. The histochemical staining solution consisted of 1 mM naphthol AS-MX phosphate, 0.05 M Tris, pH 8.5, 0.15 M NaCl, 5 mM $MgCl_2$, and 0.5 mg/ml Fast Blue BB. The stained cells were then washed with cold (4° C.) 70% ethanol, followed by centrifugation to remove the ethanol. The cells were resuspended in a second staining solution (fluorescamine) comprising 5 mg fluorescamine/liter of dry acetone. When assayed by flow cytometry, cells containing alkaline phosphatase were not fluorescent, while tumor cells were highly fluorescent. The entire assay was completed in less than three hours.

EXAMPLE 4

A bladder cell culture was assayed for alkaline phosphatase deficiencies. The procedure followed was identical to that outlined in Example 3, except the second staining solution employed was chromomycin A#3, comprising 10 mg chromomycin A3, 1.5 g $MgCl_2$ in 500 ml distilled water. When assayed by flow cytometry, cells containing alkaline phosphatase were not fluorescent, while tumor cells were highly fluorescent. Again, the assay was completed in less than three hours.

EXAMPLE 5

Neutrophils are a constant source of contamination in cervical cytology samples. Standard automated cytology employs DNA fluorescence to distinguish displastic cells from normal ones. However, neutrophils also contain DNA and add to the background signal, making results difficult to interpret.

A culture of cervical cells was centrifuged and resuspended in isotonic saline buffered with 0.02 M sodium phosphate at pH 7.0. The cells were again centrifuged and the solution removed, followed by resuspension in a fixative solution of 0.2% glutaraldehyde in the phosphate-buffered saline for 30 minutes at 4° C. The cells were then removed from the fixative solution by centrifugation and resuspension in 1 ml of phosphate-buffered saline. 0.2 ml of the cell suspension was removed and stained with a histochemical staining solution comprising hydrogen peroxide and tetramethylbenzidine. The stained cells were then washed with cold (4° C.) 70% ethanol, followed by centrifugation to remove the ethanol. The cells were then resuspended in a second staining solution of chromomycin A#3. When assayed by flow cytometry, the squamous cervical cells were strongly fluorescent, while the neutrophils exhibited very weak fluorescence. The assay was completed in less than three hours.

EXAMPLE 6

Intestinal epithelial cells consist of differentiated villus cells and cycling crypt cells. The villus cells are no longer a part of the cycling cells, however, on the basis of DNA analysis, cause major contamination to the DNA profile of the cycling crypt cells. The villus cells, however, because they are differentiated, contain a number of enzymes in abundance not found in crypt cells. Such enzymes include alkaline phosphatase and leucine aminopeptidase.

A culture of intestinal epithelial cells was centrifuged, resuspended in isotonic saline buffered with 0.02 M sodium phosphate at pH 7.0. The cells were again centrifuged and the solution removed, followed by resuspension in a fixative solution of 0.2% glutaraldehyde in the phosphate-buffered saline for 30 minutes at 4° C. The cells were then removed from the fixative solution by centrifugation and resuspension in 1 ml of phosphate-buffered saline. 0.2 ml of the cell suspension was removed and stained with a histochemical staining solution comprising 1 mM naphthol AS-MS phosphate, 0.005 M Tris, pH 8.5, 0.15 M NaCl, 5 mM $MgCl_2$, and 0.5 mg/ml Fast Blue BBN. The stained cells were then washed with cold (4° C.) 70% ethanol, followed by centrifugation to remove the ethanol. The cells were then resuspended in a second staining solution of chromomycin A#3. When assayed by flow cytometry, only the crypt cell DNA profile exhibited fluorescence. Again, the assay was completed in less than three hours.

The foregoing description of a preferred embodiment of the invention has been presented for purposes of illustration and description. It is not intended to be exhaustive or to limit the invention to the precise form disclosed, and obviously many modifications and variations are possible in light of the above teaching. For example, cell deficiencies of carbohydrates, DNA, proteins, and lipids can also be determined utilizing the method as disclosed herein. The embodiment was chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

I claim:

1. A method for assaying a cell culture for mutagenesis, comprising:
   staining said culture with a histochemical stain, said stain staining only normal cells and not abnormal cells in said culture;
   counterstaining said culture with a fluorescent stain, wherein said fluorescent stain transmits wavelengths in the wavelength region absorbed by said histochemical stain;
   subjecting said counterstained culture to exciting light; and
   detecting the fluorescence from said counterstained culture.

2. The method for assaying a cell culture for mutagenesis as defined in claim 1, wherein said fluorescence from said counterstained culture is detected in a flow cytometer.

3. A method for assaying a cell culture for mutagenesis characterized by abnormal cells being deficient in a cellular compound found in normal cells, comprising:

applying a histochemical staining solution to said culture, said histochemical stain staining only said normal cells and causing said normal cells to become colored;

counterstaining said culture with a fluorescent staining solution, said fluorescent stain staining said normal and abnormal cells wherein said fluorescent stain transmits wavelengths in the wavelength region absorbed by said histochemical stain, thereby, (but) yielding substantially detectable fluorescence only from said abnormal cells;

subjecting said counterstained culture to exciting light; and detecting the fluorescence from said abnormal cells.

4. The method for assaying a cell culture for mutagenesis as defined in claim 3, wherein said fluorescence from said abnormal cells is detected in a flow cytometer.

5. The method for assaying a cell culture for mutagenesis defined in claim 3, wherein said histochemical staining solution is selected from the group consisting of nitroblue tetrazolium, tetranitro blue tetrazolium, thiocarbmyl nitroblue tetrazolium, distyral nitroblue tetrazolium, fast blue B, fast blue BBN, fast red TR, and tetramethylbenzidine; and said fluorescent staining solution is selected from the group consisting of fluorescamine, fluorescein isothiocyanate, chromomycin A3, propidium iodide, and acridine orange.

6. The method for assaying a cell culture for mutagenesis defined in claim 3, wherein said histochemical staining solution is selected from the group consisting of nitroblue tetrazolium with phenazine methosulfate, fast blue BBN with naphthol AS-BI phosphate, and hydrogen peroxide with tetramethylbenzidine; and said fluorescent staining solution is selected from the group consisting of chromomycin A3 and fluorescamine.

7. A method for assaying Chinese hamster ovary cells for mutagenesis, comprising:

applying a solution of nitroblue tetrazolium and phenazine methosulfate to a cell culture of Chinese hamster ovary cells;

counterstaining said cell culture with a solution of chromomycin A3 or fluorescamine.

subjecting said counterstained cell culture to exciting light to produce fluorescence in abnormal cells; and detecting said fluorescence.

8. A method for assaying bladder cells for an alkaline phosphatase deficiency, comprising:

applying a solution of naphthol AS-BI phosphate with fast blue BBN to a cell culture of bladder cells;

counterstaining said cell culture with a solution of fluorescamine or chromomycin A3;

subjecting said counterstained cell culture to exciting light to produce fluorescence in cells deficient in alkaline phosphatase; and detecting said fluorescence.

9. A method of assaying a cervical cell culture for squamous cells, comprising:

applying a solution of hydrogen peroxide and tetramethylbenzidine to said cell culture;

counterstaining said cell culture with a solution of chromomycin A3;

subjecting said counterstained cell culture to exciting light to produce fluorescence in said squamous cells; and detecting said fluorescence.

10. A method of distinguishing and assaying villus and cycling crypt cells in an intestinal epithelial culture, comprising:

applying a solution of naphthol AS-MX phosphate and fast blue BBN to said cell culture;

counterstaining said cell culture with a solution of chromomycin A3;

subjecting said counterstained cell culture to exciting light to produce fluorescence in said crypt cells; and detecting said fluorescence.

* * * * *

UNITED STATES PATENT AND TRADEMARK OFFICE
CERTIFICATE OF CORRECTION

PATENT NO. : 4,345,027
DATED : August 17, 1982
INVENTOR(S) : Frank A. Dolbeare

It is certified that error appears in the above-identified patent and that said Letters Patent is hereby corrected as shown below:

On the title page of the patent, the Attorney, Agent or Firm should be changed to -- Paul Davis; Roger S. Gaither; Richard G. Besha --.

Column 1, line 34, delete "Nat." and substitute therefor -- Nat'l. --

Column 1, line 38, delete "mm" and substitute therefor -- nm --.

Column 5, line 64 delete "A#3" and substitute therefor -- A3 --.

*Signed and Sealed this*

*Seventh* Day of *June 1983*

[SEAL]

Attest:

DONALD J. QUIGG

*Attesting Officer*     *Acting Commissioner of Patents and Trademarks*